United States Patent
Krieg et al.

(10) Patent No.: US 9,242,023 B2
(45) Date of Patent: Jan. 26, 2016

(54) FORMED LYOCELL ARTICLES FOR SELECTIVE BINDING OF MONOVALENT HEAVY METAL IONS, ESPECIALLY THALLIUM AND CESIUM IONS AND RADIOACTIVE ISOTOPES THEREOF

(71) Applicant: THUERINGISCHES INSTITUT FUER TEXTIL-UND KUNSTSTOFF-FORSCHUNG E.V., Rudolstadt (DE)

(72) Inventors: Marcus Krieg, Weimar (DE); Martin Sellin, Altenberga (DE); Michael Mooz, Saalfelder Hoehe (DE)

(73) Assignee: THUERINGISCHES INSTITUT FUER TEXTIL-UND KUNSTSTOFF-FORSCHUNG E.V., Rudolstadt (DE)

( * ) Notice: Subject to any disclaimer, the term of this patent is extended or adjusted under 35 U.S.C. 154(b) by 0 days.

(21) Appl. No.: 13/849,493

(22) Filed: Mar. 23, 2013

(65) Prior Publication Data

US 2013/0295197 A1    Nov. 7, 2013

(30) Foreign Application Priority Data

Mar. 26, 2012 (DE) .......... 10 2012 005 947

(51) Int. Cl.
| | |
|---|---|
| *B01J 20/02* | (2006.01) |
| *A61L 26/00* | (2006.01) |
| *B01J 20/24* | (2006.01) |
| *B01J 20/28* | (2006.01) |
| *B01J 20/30* | (2006.01) |
| *C02F 1/28* | (2006.01) |
| *C02F 1/62* | (2006.01) |
| *B01D 53/02* | (2006.01) |
| *D01F 1/10* | (2006.01) |
| *D01F 2/00* | (2006.01) |
| *C02F 1/68* | (2006.01) |
| *C02F 101/00* | (2006.01) |
| *C02F 101/20* | (2006.01) |

(52) U.S. Cl.
CPC .......... *A61L 26/0066* (2013.01); *A61L 26/0095* (2013.01); *B01D 53/02* (2013.01); *B01J 20/0229* (2013.01); *B01J 20/0274* (2013.01); *B01J 20/24* (2013.01); *B01J 20/28023* (2013.01); *B01J 20/28026* (2013.01); *B01J 20/28028* (2013.01); *B01J 20/3007* (2013.01); *C02F 1/28* (2013.01); *C02F 1/286* (2013.01); *C02F 1/62* (2013.01); *D01F 1/10* (2013.01); *D01F 2/00* (2013.01); *B01J 2220/46* (2013.01); *B01J 2220/4831* (2013.01); *C02F 1/683* (2013.01); *C02F 2101/006* (2013.01); *C02F 2101/20* (2013.01)

(58) Field of Classification Search
CPC .......... D01F 2/02; C02F 2101/20; C02F 1/28; C02F 2101/006; A61L 26/0095; B01D 53/02; B01J 2220/4831; B01J 20/28028; B01J 20/0229
See application file for complete search history.

(56) References Cited

U.S. PATENT DOCUMENTS

| | | | | |
|---|---|---|---|---|
| 5,407,889 A | * | 4/1995 | Remes | ............ G21F 9/12 |
| | | | | 502/400 |
| 5,601,722 A | | 2/1997 | Tanihara | |
| 6,093,664 A | * | 7/2000 | White et al. | ............ B01J 20/04 |
| | | | | 210/502.1 |

FOREIGN PATENT DOCUMENTS

| | | |
|---|---|---|
| DE | 848 685 C | 9/1952 |
| DE | 37 35 304 A1 | 5/1989 |
| DE | 44 26966 C2 | 4/1997 |
| DE | 696 08 820 T2 | 11/2000 |
| EP | 0 575 612 A1 | 12/1993 |
| NL | 9401686 A | 5/1996 |
| RU | 2021009 C1 | 10/1994 |
| RU | 2 033 240 C1 | 4/1995 |
| RU | 2111050 C1 | 5/1998 |
| RU | 2437177 C1 | 12/2011 |
| SU | 1769947 A1 | 10/1992 |

OTHER PUBLICATIONS

Article definition. (http://www.merriam-webster.com/dictionary/article); accessed Nov. 13, 2013.*
Tencel Lyocell Short-Cut Fiber ("Tencel" http://www.eftfibers.com/prod_lyocell.php); published online 2010; accessed Nov. 13, 2013.*
Strelko et al. Zhurnal Prikladnoi Khimii 1998, 71, 8, 1295-1297.*
Machine translation of Strelko, 1998, translated Nov. 2013.*
Kawamura, S. et al. "A rapid separation of sodium, potassium, rubidium and caesium by thin layer chromatography on zinc ferrocyanide" J. Chromatog., 26 (1967) pp. 557-560.
Remez, V. P. et al.,"The Rapid Determination of Caesium Radionuclides in Water Systems Using Composite Sorbents" Appl. Radiat. Isot. vol. 47, No. 9/10, (1996) pp. 885-886.

* cited by examiner

Primary Examiner — Sean Basquill
Assistant Examiner — Andrew S Rosenthal
(74) Attorney, Agent, or Firm — ProPat, L.L.C.

(57) ABSTRACT

Shaped lyocell cellulose articles are provided for binding heavy metal ions and radioactive isotopes thereof. The shaped articles include one or more hexacyanoferrates that are incorporated in a cellulosic matrix and uniformly distributed therein. The shaped articles can be fibers, fibrids, fibrous nonwoven webs, granules, beads, self-supporting films, tubular films, filaments, sponges, foams or bristles. They are useful for water treatment and water decontamination, for metal beneficiation, for treatment of wound with wound dressings, for air and gas filtration and in protective apparel.

20 Claims, 2 Drawing Sheets

1a
1b
1c 2a  2b

FORMED LYOCELL ARTICLES FOR SELECTIVE BINDING OF MONOVALENT HEAVY METAL IONS, ESPECIALLY THALLIUM AND CESIUM IONS AND RADIOACTIVE ISOTOPES THEREOF

CROSS-REFERENCE TO RELATED APPLICATIONS

This application claims priority to German Patent Application 10 2012 005 947.7 filed Mar. 26, 2012 which is hereby incorporated herein by reference in its entirety.

FIELD OF THE INVENTION

This invention relates to shaped cellulosic articles (alternatively referred to as bodies) produced by the lyocell process and incorporating a homogeneous distribution of particles in the cellulose matrix thereof.

BACKGROUND OF THE INVENTION

It is known to use the compounds from the group of hexacyanoferrates to remove different isotopes of heavy metal ions of the elements cesium, strontium, thallium, cadmium and lead from aqueous systems. The hexacyanoferrates used are advantageously immobilized in a supporting material so as to prevent them passing into the aqueous or moist gaseous phase surrounding the material. Known supporting materials for hexacyanoferrates are porous materials, such as ion exchange resins, sawdust, wood-base materials, fiber pulp materials, paper, natural fibers or regenerated cellulose fibers. Enrichment is always purely surficial. The uptake capacity of such supporting materials for hexacyanoferrates is limited by their surface area and pore structure.

It is known to use compounds from the group of hexacyanoferrates to remove heavy metal ions of the elements cesium, strontium, thallium, cadmium and lead from aqueous systems. Hexacyanoferrates bind the recited heavy metal ions by ion exchange and incorporation in their ionic lattice. The group of hexacyanoferrates is made up of electrically neutral compounds which are comprised of the negatively charged hexacyanoferrate anion and positively charged counter-ions, preferably metal cations.

Preference among this group is given to the use of representatives which are sparingly soluble in water. Typical examples are Prussian blue $Fe_4[Fe(CN)_6]_3$ or $A_xB_y[Fe(CN)_6]$ (A=$NH_4$/Li/Na/K, B=Fe/Ni/Co/Cu/Ti/Cr). The patent DE 3735304 and the IAEA Report "The use of Prussian Blue to reduce radiocaesium contamination of milk and meat produced on territories affected by the Chernobyl accident" of February 1997 describe the use of hexacyanoferrates to bind $Tl^+$ and $Cs^+$ isotopes in human and veterinary medicine. The orally administered hexacyanoferrates are secreted again by the body. These uses require no separation or supportation, so pure hexacyanoferrates can be used. When hexacyanoferrates are used to remove heavy metal ions from aqueous systems, however, it is desirable for these to be completely separated from the system. The insoluble microcrystalline hexacyanoferrates such as $NH_4Fe[Fe(CN)_6]$ or $Fe_4[Fe(CN)_6]_3$ form colloidal solutions in water.

Colloidal particle sizes between 1 and 100 μm and below 1 μm limit the use of pure hexacyanoferrates in filter layers. Filter layers comprising hexacyanoferrates of this type are associated with substantial pressure drops over the length of the filter bed. The colloidal solubility further leads to a drag-out of the hexacyanoferrate even through barriers having pore sizes of less than 0.1 μm.

EP 0 575 612 A1 describes porous, particulate or fibrous supporting materials which have been treated with a suspension of hexacyanoferrates. The supporting materials thus treated bind radioactive cesium, rubidium and strontium ions in particular. The attempt to load cellulose fibers, especially lyocell cellulose fibers, with hexacyanoferrates revealed several disadvantages. The fibers could only be loaded with a limited amount of hexacyanoferrates. The hexacyanoferrate particles moreover displayed low adherence and so were easily washed off. The poor adherence of the hexacyanoferrate particles to the cellulose fibers moreover led to dusting in the course of processing. The distribution of the hexacyanoferrate particles on the fibers was also not homogeneous.

The problem addressed by the present invention is therefore that of incorporating hexacyanoferrates such as $NH_4Fe[Fe(CN)_6]$ or $Fe_4[Fe(CN)_6]_3$ in a matrix, ideally without impairing their ability to adsorb or absorb particular heavy metal ions, and thus preventing the formation of colloidal solutions. The incorporated hexacyanoferrates shall be firmly attached in the matrix and form a homogeneous distribution therein. The corresponding shaped articles shall be useful as filter material having high uptake capacity for heavy metal ions.

Various methods and solutions have been described for this problem, which all have disadvantages.

One proposed solution to the stated problem is to fix hexacyanoferrates to ion exchange materials. Thus, EP1419009 utilizes a composite material based on a supporting material having a coating of ion exchange material to effect ionic fixing.

RU2033240 further describes binding hexacyanoferrate to viscose fibers with ion exchanger functionalization. Even porous natural materials such as sawdust are stated by EP575612 to be capable of sorbing and hence binding hexacyanoferrates. With ionic fixation, displacement off the ion exchanger by other ions is possible. Surficially coated porous supporting materials, by contrast, are known to have limits with regard to adherence and mechanical stability.

A further approach to solving the stated problem is based on the idea of insoluble hexacyanoferrates being generated, and hence fixed, in the pores of porous supporting materials. This method is adopted in U.S. Pat. No. 5,601,722. Disadvantages here are that the method needs several individual steps for the synthesis and that the binding to the support is purely mechanical only. A further disadvantage is that the sorption kinetics of heavy metal ions are constrained by the degree of accessibility to the inner region of the pore structure.

Accordingly, there continues to be a need for shaped cellulose articles for selective binding of monovalent heavy metal ions, especially thallium and cesium ions and radioactive isotopes thereof.

SUMMARY OF ADVANTAGEOUS EMBODIMENTS OF THE INVENTION

We have found that, surprisingly, hexacyanoferrates such as $NH_4Fe[Fe(CN)_6]$ or $Fe_4[Fe(CN)_6]_3$ can be directly integrated into shaped cellulosic articles and so are resistant to leaching. The production process is such that the hexacyanoferrate used becomes uniformly distributed in and fully enclosed by the cellulose support. A composite material of this kind is not inferior to the pure hexacyanoferrate in its ability to sorb heavy metal ions such as thallium or cesium in an aqueous medium. This is attributable to the swellability and porosity of the cellulose matrix in aqueous systems, which ensure good access to the hexacyanoferrate for the heavy metal ions. The composite material of the present invention is a solution for the desired use to bind heavy metal ions in aqueous systems. The composite material is produced directly from the desired hexacyanoferrate and the cellulosic support. It is notable for a homogeneous distribution of the hexacyanoferrate in the matrix. There is no significant reduction in the adsorbability of the hexacyanoferrate due to incorporation in the matrix. There is no release of hexacyanoferrates from the matrix due to aqueous media.

DETAILED DESCRIPTION OF ADVANTAGEOUS EMBODIMENTS OF THE INVENTION

Figure 1:
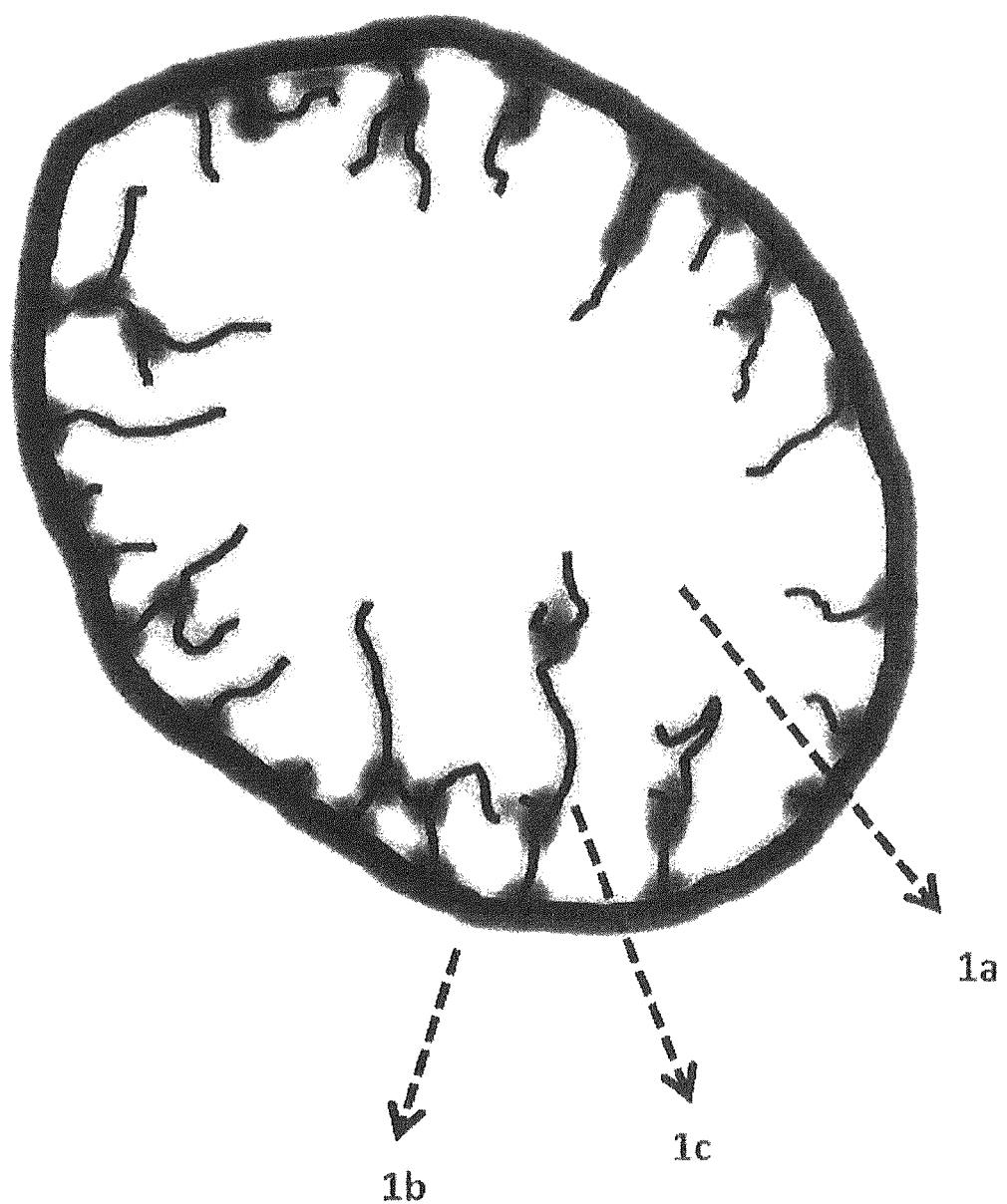
FIG. 1 is a schematic illustration of a cross section through a lyocell fiber laden with hexacyanoferrates formed by the known prior art process of drenching or impregnating.

The composition described, which is referred to herein as composite material, of cellulose and hexacyanoferrate combines secure supportation of an active hexacyanoferrate with a high level of loading while preserving the desired ability to bind heavy metals.

The composite material is notable for a uniform distribution of the hexacyanoferrate particles throughout the entire cross section. The access of heavy metal ions to the hexacyanoferrates is ensured by the swellability of the cellulosic supporting material. A composite material of this kind is obtained by regenerating a cellulose solution with suspended hexacyanoferrate particles in water.

Depending on its application, the composite material is a self-supporting film, a fiber, a bristle, a granule, a fibrid, a membrane, a foam or a spunbonded web or else a derived manifestation such as a fibrous nonwoven web fabric, a woven fabric, a loop-formingly knit fabric, a loop-drawingly knit fabric, or paper.

The production of shaped cellulose articles with integrated functional additives is established art and can be realized by regenerating cellulose solutions or cellulose derivatives comprising admixed additives.

Established processes include, for instance, the viscose process, the cuoxam process and the lyocell process involving tertiary amine oxides. A dry/wet spinning process, such as described in DE 44 26 966 C2, can be used to produce yarns and self-supporting films in lyocell cellulose which contain a high proportion of added substances. The cellulose is dissolved purely physically in a suitable solvent, such as N-methylmorpholine N-oxide monohydrate. The added substances are then finely distributed in the solution. The mixture is then formed into yarns or self-supporting films. The solvent is then removed in a water bath to obtain shaped cellulose articles with enclosed and thus fixed solids. Yet because hexacyanoferrates such as $NH_4Fe[Fe(CN)_6]$ or $Fe_4[Fe(CN)_6]_3$ have low stability to acids and alkalis, these production processes must be ruled out. The customary solvents and coagulation media of the lyocell process and the prevailing processing conditions give rise to incompatibilities between the Prussian blue and the solution and/or coagulation medium.

We have found that, surprisingly, the composite material described can be obtained with alternative solvents for cellulose. Success is achieved in particular when the cellulose is dissolved and regenerated without having to use acidic or alkaline conditions. This is the case with the use of solvent systems such as ionic liquids, DMSO/TBAF, LiCl/DMAc, LiCl/DMF. The composite material described is obtainable using an ionic liquid, in particular with 1-butyl-3-methylimidazolium chloride, with regeneration in pure water. In general, production by dissolving cellulose with cellulose solvents and by regenerating in nonsolvents for cellulose, particularly water, is possible as long as operationally needed acids and bases do not lead to a change in or destruction of the hexacyanoferrates. By operating the lyocell process with selected ionic liquids as solvents, it has become possible for the first time to incorporate Prussian blue homogeneously in regenerated cellulose fibers and to produce shaped lyocell articles having a high loading of hexacyanoferrate particles.

The present invention accordingly provides shaped lyocell cellulose articles for binding heavy metal ions and radioactive isotopes thereof, wherein one or more hexacyanoferrates are incorporated in a cellulosic matrix and uniformly distributed therein.

The hexacyanoferrate is preferably a neutral-charge chemical compound comprised of hexacyanoferrate anions and cations, preferably cobalt, copper, sodium, potassium or ammonium and more preferably iron, having particle sizes between 0.001 µm and 100 µm and preferably between 0.1 µm and 50 µm.

The shaped articles produced by following a process of this type are hereinafter referred to as shaped lyocell cellulose articles. Shaped cellulosic articles are obtained in the lyocell process via a solution spinning process with organic solvents or mixtures of organic solvents and water, without derivatization of the cellulose (terminology as per BISFA 2009). The term "shaped article" in connection with the present invention refers to fibers, fibrids, fibrous nonwoven webs, granules, beads, self-supporting films, tubular films, filaments, sponges, foams and bristles, while textile-processable fibers are preferred.

We have found that, surprisingly, the shaped lyocell cellulose articles of the present invention, comprising a homogeneous distribution of hexacyanoferrate particles throughout the matrix, have a high sorption capacity for monovalent heavy metal ions, especially thallium and cesium ions and radioactive isotopes thereof. Although the hexacyanoferrate particles are fully enclosed in a polymeric matrix, sorption capacity was unexpectedly not observed to decrease. The sorption capacity of shaped lyocell cellulose articles according to the present invention is on the same order of magnitude as the sorption capacity of a comparable amount of hexacyanoferrate powder not bound to a polymer.

The shaped lyocell cellulose articles described can contain different particle sizes of the hexacyanoferrates. According to the present invention, the dimensions of the shaped lyocell cellulose article are greater than those of the hexacyanoferrate particles used. Even hexacyanoferrates less than 1 µm in diameter become uniformly distributed in the matrix and the formation of colloidal solutions in adjoining aqueous phases is prevented. Depending on the thickness of the shaped lyocell cellulose article, hexacyanoferrate crystallites having diameters from 1 µm to 100 µm and less than 1 µm can be processed. This makes it possible to improve the sorption kinetics for heavy metal ions with decreasing particle diameter.

The production process used allows very low weight fractions of <1% hexacyanoferrate, based on the composite material, and high weight fractions up to 80% hexacyanoferrate, based on the shaped lyocell cellulose article. The proportion of hexacyanoferrates is preferably in the range from 0.1 to 80 wt % and more preferably in the range from 10 to 50 wt % relative to the overall composition. The production process can be engineered as a simple, one-step operation.

The cellulosic matrix of the shaped lyocell cellulose article described can be 100% cellulose. The cellulosic matrix can further be made up of a mixture of more than 50 wt % cellulose with polymeric additives, such as cellulose derivatives, and particulate additives, such as carbon black, activated carbon, ion exchange resin, inorganic pigments and salts.

The production process used enables the production of different manifestations of the shaped lyocell cellulose article. Depending on the intended use, the direct forming preferably as fibrid, fiber, spunbonded web, beads, granules, self-supporting film, tubular film, filament, sponge or bristle is established art. The further processing of one of the recited manifestations into a fibrous nonwoven web fabric, a woven fabric, a loop-formingly knit fabric, a loop-drawingly knit fabric, paper or other products that contain the shaped lyocell cellulose article described in proportions of 1 to 100% is likewise possible.

Despite the incorporation of hexacyanoferrate in a cellulosic matrix, separation of matrix and hexacyanoferrate is possible. This enables recycling of the hexacyanoferrates, subjecting the pure hexacyanoferrates to recovery of the bound heavy metals or a weight reduction in land filling. For this, the cellulosic matrix can be dissolved by known solvents for cellulose, decomposed by acids, converted into a cellulose derivative by chemical reactions, or be decomposed by composting.

In the shaped cellulosic articles of the present invention, produced by the lyocell process, the hexacyanoferrates are firmly attached in a polymeric matrix and hence resistant to leaching into an aqueous solution. Owing to this attachment, the composite material is very useful in filter applications. It provides easy separation after use without the employment of centrifuges and filters. This can only be successful when the shaped lyocell cellulose article prevents the colloidally water-soluble hexacyanoferrates passing into the aqueous phase. The described attachment of the hexacyanoferrates does not impair their ability to bind heavy metal ions. The described attachment of hexacyanoferrates is particularly suitable for these objects. The cellulosic polymeric matrix gives the heavy metal ions good access to the active hexacyanoferrates by swelling with water. The direct forming of the starting materials into the shaped lyocell cellulose article results in a uniform distribution of the hexacyanoferrates throughout the entire cross section. The hexacyanoferrates are further fully surrounded by the polymeric matrix. Losses of hexacyanoferrate due to mechanical effects or due to detachment from surfaces are diminished as a result.

The shaped lyocell cellulose article of the present invention is notable for a high variety of possible shapes and the usefulness associated therewith. Different uses are apparent depending on whether the article is formed into self-supporting film, fiber, bristle, granule, fibrid or spunbonded web. The use as filter material in a liquid and moist environment to absorb heavy metal ions is of particular interest. This includes for example the purification of water having thallium and cesium contamination or the beneficiation, separation or recovery of these elements from aqueous solutions or process steams. This also includes the possibility of using the composite material for thallium and cesium detoxification of organisms. Compared with pure hexacyanoferrate, the shaped lyocell cellulose article gives the option of modifying a drug release profile or the possibility of external application with wound dressings. Preferably, the capacity for the binding of heavy metal ions, especially thallium and cesium ions, is between 20% and 400% and particularly between 75% and 200%, based on the hexacyanoferrate present and compared with the pure hexacyanoferrate.

The shaped lyocell cellulose article is further useful for the filtration of vapors and also aerosols and hence for filtration of gases and air. In this use of the shaped lyocell cellulose article, it is the ability of the cellulosic matrix to imbibe and retain moisture which enables heavy metal contamination to be taken up from such media as well. Hence it is also possible to use this shaped lyocell cellulose article to equip respirators and personal protective apparel.

The object of the shaped lyocell cellulose article is achieved not only by the type of possible forms mentioned but also by the further processing of these forms. This includes for example the conversion or addition of shaped lyocell cellulose articles to beds, millbases, wovens, formed-loop knits, drawn-loop knits, papers or fibrous nonwoven webs.

Figure 2:
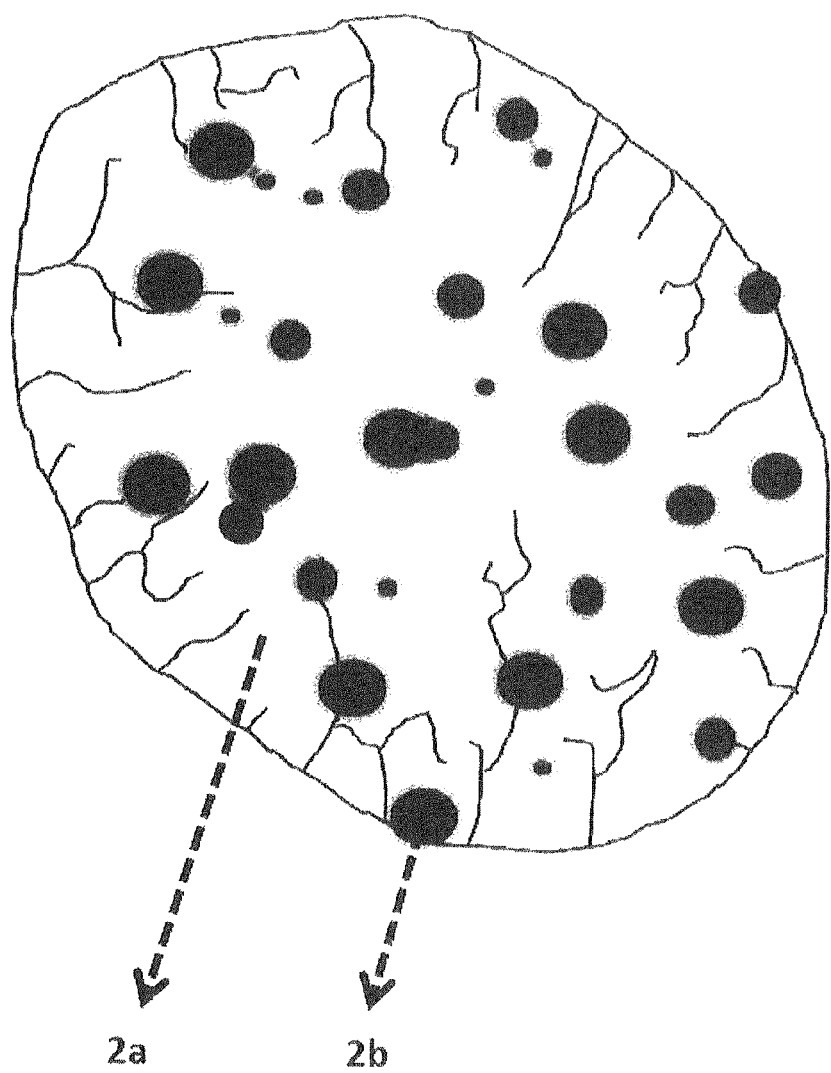
FIG. 2 is a schematic illustration of a cross section through a lyocell fiber laden with hexacyanoferrates formed in accordance with this invention.

The invention will now be more particularly described with reference to drawings, where FIG. 1 shows a cross section through a lyocell fiber laden with hexacyanoferrates by the known process of drenching or impregnating in accordance with EP 0 575 612 A1, FIG. 2 shows a cross section through a lyocell fiber laden with hexacyanoferrates in accordance with this invention.

The fiber cross section depicted in FIG. 1 consists of a porous lyocell matrix $1a$. The surface of this lyocell matrix evinces a coating with hexacyanoferrates $1b$ and hexacyanoferrate-filled pores $1c$.

The fiber cross section depicted in FIG. 2 consists of a porous lyocell matrix $2a$. This lyocell matrix contains hexacyanoferrates $2b$. The hexacyanoferrates are uniformly distributed throughout the entire cross section and are surrounded by the lyocell matrix.

The examples which follow illustrate the invention. Percentages are by weight unless otherwise stated or evident from the context.

EXAMPLE 1

A hexacyanoferrate $Fe_4[Fe(CN)_6]_3$ prepared for selective sorption of thallium and cesium was pulverized using a mortar and sieved through a small-mesh sieve to remove particle sizes 40 µm in size or larger. The material obtained with a particle size less than 40 µm ($x_{90}$=31.9 µm, $x_{50}$=10.36 µm) was subsequently processed with cellulose into a cellulose film having a diameter of 100 µm and a loading of 10 wt % of hexacyanoferrate.

A mixture of 165 g of water, 386 g of 1-butyl-3-methylimidazolium chloride, 27 g of ground cellulose having a degree of polymerization (DP) of 615 and 3 g of the hexacyanoferrate was prepared. This mixture is homogenized using an ULTRATURRAX® and then treated in a planetary stirrer by shearing and heating at a vacuum of 10 mbar and at a maximum temperature of 105° C. The result obtained was a homogeneous mixture containing 9% of cellulose, 1% of hexacyanoferrate, 89.9% of 1-butyl-3-methylimidazolium chloride and 0.1% of water.

This mixture was spread into a thin layer and stored in a water bath to coagulate the cellulose and to wash off the solvent.

Following complete coagulation, the composite material was obtained in the form of a film having a thickness of 30 µm.

This deep blue film containing 10 wt % of hexacyanoferrate was dried on a tenter. The residual moisture content of the material is 10 wt %.

EXAMPLE 2

A hexacyanoferrate $Fe_4[Fe(CN)_6]_3$ prepared for selective sorption of thallium and cesium was ground with an opposing-jet mill to a particle size less than 7 μm ($x_{90}$=4.66 μm, $x_{50}$=2.88 μm). The material obtained was subsequently processed with cellulose into staple fibers having a linear density of 3 dtex and a loading of 10 wt % of hexacyanoferrate absolute.

A homogeneous mixture was prepared from 1654 g of water, 3860 g of 1-butyl-3-methylimidazolium chloride, 270 g of ground cellulose having a degree of polymerization (DP) of 615 and 30 g of ground hexacyanoferrate similarly to Example 1. The forming of this mixture into staple fibers was done similarly to lyocell technology for producing cellulose staple fibers.

The fiber composite material obtained was chopped to a length of 38 mm and dried at 50° C. down to a residual moisture content of 10 wt % absolute.

Parameters of staple fibers obtained in Example 2:

| | |
|---|---|
| Linear density [dtex] | 3.23 |
| Staple fiber length [mm] | 38 |
| Fiber tenacity [cN/tex] | 37.7 |
| Loop tenacity [cN/tex] | 5.24 |
| Elongation at break [%] | 10.8 |

EXAMPLE 3

Suitability for binding thallium and cesium in filtration applications:
100 mL of a test solution containing 0.2 mol/L of sodium chloride and 0.1 mol/L of thallium(I) nitrate or 0.1 mol/L of cesium(I) sulfate in deionized water were contacted with 1 g of the composite material or 0.1 g of the employed hexacyanoferrate for 24 hours under agitation. The sorption of thallium ions or cesium ions by the material was determined by determining the concentration of these elements in the test solution using ICP-OES after separating off the material. The binding power is reported in grams of adsorbed ion (thallium, cesium) relative to the initial weight of the material and is based on a triplicate determination in each case.

| Material | weight % of hexacyanoferrate | Sorption $Tl^+$ g/g | Sorption $Cs^+$ g/g |
|---|---|---|---|
| Example 1 $Fe_4[Fe(CN)_6]_3$ <40 μm | 100 | 0.302 | 0.279 |
| Example 1 film | 10 | 0.062 | 0.021 |
| Example 2 $Fe_4[Fe(CN)_6]_3$ <7 μm | 100 | 0.291 | 0.297 |
| Example 2 fiber | 10 | 0.032 | 0.027 |

Thallium and cesium binding capacity was accordingly only minimally affected by the incorporation in the cellulosic matrix. In some cases, binding power was observed to rise. The hexacyanoferrate in both the fiber and the film still gave a cesium sorption amounting to 75-90% of that of the pure hexacyanoferrate without matrix. A film prepared similarly to Example 1 with the <7 μm hexacyanoferrate from Example 2 even achieved 110% in cesium binding compared with the hexacyanoferrate used. The binding of thallium was increased by the incorporation in the cellulosic matrix. In Example 1, the capacity for thallium doubled compared with the pure hexacyanoferrate used. An increase in the capacity for the selective binding of thallium or cesium is a particular advantage of this shaped lyocell cellulose article. The cellulosic matrix can exert a positive effect on the total level of thallium or cesium binding. The shaped lyocell cellulose articles described (fiber, film) could be completely removed from the test solution without filtration or centrifugation. The employed hexacyanoferrate having the particle sizes <40 μm and <7 μm could only be separated from the test solution by means of repeated centrifugation and filtration with filter materials having a pore size of 0.02 μm.

That which is claimed:

1. A shaped lyocell cellulose body for binding heavy metal ions and radioactive isotopes thereof comprising a lyocell cellulosic matrix and one more hexacyanoferrates suspended inside said cellulosic matrix and uniformly distributed throughout the entire cross-section and fully enclosed by the cellulose wherein the preparation therof does not comprise alkaline or acidic conditions.

2. The shaped cellulose body as claimed in claim 1, wherein the hexacyanoferrate is a neutral-charge chemical compound comprised of hexacyanoferrate anions and of cations, said hexacyanoferrate having particle sizes between 0.001 μm and 100 μm.

3. The shaped cellulose body as claimed in claim 2, wherein the cations are cobalt, copper, sodium, potassium or ammonium.

4. The shaped cellulose body as claimed in claim 2, wherein the cation is iron.

5. The shaped cellulose body as claimed in claim 2, wherein the particle sizes are between 0.1 μm and 50 μm.

6. The shaped cellulose body as claimed in claim 1, wherein the cellulosic matrix consists either of pure cellulose or of a mixture of more than 50% cellulose with polymeric additives.

7. The shaped cellulose body as claimed in claim 6, wherein the polymeric additives are cellulose derivatives and the particulate additives are carbon black, activated carbon, ion exchange resins, inorganic pigments and/or salts.

8. The shaped cellulose body as claimed in claim 1, wherein the hexacyanoferrates comprise from 0.1 to 80 wt % of the overall composition.

9. The shaped cellulose body as claimed in claim 8, wherein the hexacyanoferrates comprise from 10 to 50 wt % of the overall composition.

10. The shaped cellulose body as claimed in claim 1, wherein the capacity for the binding of heavy metal ions is between 20% and 400%, based on the hexacyanoferrate present and compared with the pure hexacyanoferrate.

11. The shaped cellulose body as claimed in claim 10, wherein the capacity for the binding of heavy metal ions is between 75% and 200%, based on the hexacyanoferrate present and compared with the pure hexacyanoferrate.

12. The shaped cellulose body as claimed in claim 10, wherein the heavy metal ions are thallium or cesium ions.

13. The shaped cellulose body as claimed in claim 1, wherein said shaped body is a fibrid, a fiber, a fibrous nonwoven web, a granule, a bead, a self-supporting film, a tubular film, a filament, a sponge or a bristle.

14. A filter material comprising the cellulose body of claim 1, wherein said celluose body is present in a proportion of more than 1 wt %, based on the total weight of the material.

15. A method of adsorbing monovalent metal ions comprising swelling the shaped cellulose body as claimed in claim 1 to provide access to the active hexacyanoferrate and adsorbing monovalent metal ions in aqueous or moist systems.

16. The method as claimed in claim 15, wherein the metal ions are thallium, cesium or isotopes thereof.

17. The method as claimed in claim 15, wherein said method is a method of water treatment, water decontamination, metal beneficiation, wound treatment with wound dressings, air filtration, gas filtration or protection comprising apparel.

18. The shaped lyocell cellulose body of claim 1 wherein said shaped body is a solution spun article.

19. The shaped lyocell cellulose body of claim 1 wherein said shaped body is a fiber or film formed from said lyocell cellulosic matrix.

20. The shaped lyocell cellulose body of claim 19 wherein said body exhibits an increased capacity for thallium binding compared with the hexacyanoferrate alone and wherein there is no release of hexacyanoferrates from the matrix due to aqueous media.

* * * * *